United States Patent [19]
Kross

[11] Patent Number: 6,126,961
[45] Date of Patent: Oct. 3, 2000

[54] COMPOSITION AND METHOD FOR REDUCING THE COLONIZATION OF ANIMAL INTESTINES BY SALMONELLA AND OTHER BACTERIAL PATHOGENS

[76] Inventor: Robert D. Kross, 2506 Florin Ct., Bellmore, N.Y. 11710

[21] Appl. No.: 09/059,161

[22] Filed: Apr. 13, 1998

[51] Int. Cl.[7] ....................................................... A23K 1/18
[52] U.S. Cl. ............................. 424/442; 426/807; 514/54
[58] Field of Search .................................. 424/405, 438, 424/442; 426/807; 514/54

[56] References Cited

U.S. PATENT DOCUMENTS

| | | | |
|---|---|---|---|
| 4,134,973 | 1/1979 | Fisher et al. | 424/180 |
| 5,217,740 | 6/1993 | Lanter | 426/573 |
| 5,721,271 | 2/1998 | Banks et al. | 514/450 |
| 5,840,704 | 11/1998 | Gibson et al. | 514/30 |

OTHER PUBLICATIONS

Ohya et al., *World Patent Index,* vol. 93, #287629, 1993.

*Primary Examiner*—Robert H. Harrison
*Attorney, Agent, or Firm*—Edwin D. Schindler

[57] ABSTRACT

An animal feed composition for reducing colonization of animal intestines by Salmonella and other bacterial pathogens, includes a polysaccharide containing cis-hydroxy sugar units or a derivative thereof, or the monosaccharide ribose or rhamnose, or a derivative thereof, and an animal feed. The polysaccharide cis-hydroxy sugar units may be one or more of mannose, a mannose derivative, galactose, a galactose derivative, galactomannans, galactosamine, fucose and arabinose. The polysaccharides may be incorporated into an animal feed in the form of a food gum or other biolpolymer.

20 Claims, No Drawings

COMPOSITION AND METHOD FOR REDUCING THE COLONIZATION OF ANIMAL INTESTINES BY SALMONELLA AND OTHER BACTERIAL PATHOGENS

TECHNICAL FIELD

This patent relates to the reduction or elimination of pathogenic bacteria in the intestinal tracts of poultry and mammals as a result of the incorporation of certain naturally-occurring polymers in the animals' feed. It is more specifically directed to the use of polysaccharides containing sugar units of preferred spatial configurations, which structures promote their adhesion to receptor sites on the surfaces of the pathogens and their subsequent physical elimination from the animals' gut.

BACKGROUND OF THE INVENTION

Poultry and meat are frequent sources of foodborne disease organisms. The pathogens associated with poultry products include Salmonella spp., *Listeria monocytogenes, Escherichia coli* and *Campylobacter jejuni*. These microorganisms are introduced into poultry and animal flocks during raising and onto carcasses during processing. These bacteria colonize the mucus covering gut surfaces and can also be found in deep mucus of intestinal crypts. The bacterial surfaces have specific adhesins or insertional structures which attach to the caudal ileum and ceca, and thereby resist abrasive loss by food materials which transit the intestine.

A variety of chemical agents and physical processes have been employed, with varying success, to remove and/or destroy some of the pathogenic organisms which transfer to meat and poultry surfaces during the processing of their carcasses. These include trisodium phosphate, chlorine, chlorine dioxide, organic acids, hydrogen peroxide, acidified sodium chlorite and steam. Despite the intervention of these materials and processes, for example, it is estimated that close to 25% of current poultry carcasses that reach US consumers contain Salmonella organisms. A number of recent outbreaks of infections and death caused by the specific *E. coli* strain 0157:H7 have occurred, as a result of contaminated beef.

Recent attention has been directed to reducing the colonization of poultry intestinal tracts by these pathogens, so that the subsequent processing of their carcasses would not be burdened with the elimination of their current high numbers. One such approach has been termed mucosal competitive exclusion, which involves feeding new chicks bacterial cultures derived from mucosa-associated microorganisms of chicken cecal epithelia in order to surpress the growth of pathogens such as Campylobacter and Salmonella in their gut. In one evaluation of this concept, chicks that had been exposed to this bacterial combination grew to yield processed carcasses in which only 10 percent were Salmonellae positive, as compared with 41 percent for untreated flocks. In another study, the reduction was from 9.1 percent Salmonella contamination of control carcasses to 4.5 percent for treated flocks.

In a related approach, it has been discovered that the inclusion of certain monomeric and dimeric sugars in the poultry diet will reduce the levels of Salmonella organisms that colonize their gut. As previously indicated, sugar receptors on the surfaces of intestinal epithelial cells apparently serve as receptors for the binding of some bacterial pathogens. The interaction between the Gram-negative bacterial pili and these receptor can be blocked by certain simple sugars in the animal feed. When 2.5% levels of arabinose, galactose, and lactose were included in the diet of chicks, there was a significant reduction in Salmonella levels in their cecal contents up through 21 days of age, except for lactose where organism levels reverted thereafter. An earlier study showed 5% dietary levels of these sugars to be very effective. In an in vitro study, the ceca of 1-week old chicks showed reduced bacterial adhesion when contacted by the carbohydrates D-galactose, N-acetyl-D-galactosamine, L-fucose, L+arabinose and D+mannose, but this effect disappeared in 2-week old chick ceca. Finally when 1-day old chicks were fed a 2.5% mannose solution for 10 days, and then challenged with *Salmonella typhimurium*, only 31% on average showed cecal contamination, compared with an average of 84% of control birds that were not first exposed to the sugar. Another study showed that the adherence of the pathogen *Escherichia coli* to mucosal epithelial cells of mammals is mediated by mannose-specific sites on the bacterial surface, and that inclusion of mannose in the diet will interfere with *E. coli* adherence to the mammalian epithelial cells.

An adaptation of the use of simple dietary sugars for reducing Salmonella populations in poultry intestinal tracts has appeared recently in the inclusion of dried yeasts in poultry diets. Yeast cell walls include polymeric sugars such as mannans and galactomannans in their compositions, which polymers apparently function in the same manner as their component sugars, i.e. in attaching to the bacterial sites which would otherwise bind to intestinal surfaces. The disadvantage of this approach, of course, lies in the cost-inefficiency associated with use of whole yeast cells as a carrier for the specific sugar components that are present only on the yeast cell surfaces. The more the weight requirement of the feed ingredient, the more costly is the diet, as well as the possibility that the other yeast components may have adverse effects on poultry nutrition. In a recent study, dried yeast cells that were incorporated into chicks' diets were found to bring about a significant reduction in Salmonella levels of the animals' ceca.

The present invention results from an attempt to understand and identify the specificity of the binding sites associated with certain pathogen surfaces, which binding site are apparently associated with certain carbohydrate structures, and to then apply this knowledge in order to optimize the selection of those carbohydrates which most effectively and economocially reduce the levels of human pathogens in animal viscera.

OBJECTS AND SUMMARY OF THE INVENTION

Accordingly, it is a general object of the present invention to improve the current art associated with the use of certain sugars and sugar-containing structures as dietary supplements for reducing human pathogen colonization of animal intestines.

Another object of the present invention is to identify the specific structural characteristics of sugars which enables certain types to bind to surface sites of bacterial pathogens and inhibit thereby their binding to mucosal surfaces of animal intestines.

A more specific object of this invention is to provide highly efficient carbohydrate compositions which can be incorporated into the diets of animals for the safe and economical reduction of human-pathogen colonies in their intestinal tracts.

Other objects and advantages of the present invention will become apparent from the following summary of the invention and description of its preferred embodiments.

The present invention provides, in one aspect, compositions for reducing or eliminating colonies of human pathogenic organisms in the viscera of food animals. The compositions comprise certain food-grade gums, either of plant origin or elaborated by bacteria cultures, which gums are incorporated into standard animal feed and, following ingestion, provide binding surfaces for intestinal pathogens as the food bolus traverses the gastrointestinal tract. By so doing, the gums compete with the attractive sites on epithelial surfaces of the animal's gut to which the pathogens might ordinarily adhere and thrive upon.

It has been now discovered that there is a common characteristic of the various sugars, carbohydrates, gums and yeasts which predisposes these materials to serve as effective binding sites for adsorption of bacterial pathogens in competition with intestinal mucosal surfaces. The sugars and sugar-moieties of the adsorptive materials have at least one pair of vicinal hydroxyl groups, that is —OH groups attached to adjacent carbon atoms, which are sterically positioned closest to each other, rather than opposed to each other. For descriptive purposes herein, that closest position is termed "cis" in contrast to the alternate "trans" designation for sterically opposed OH's. Included in this group of cis-hydroxy sugars, and the polymers formed therefrom are, among others, mannose and mannan polymers, galactose, galactomannans and galactosamine, arabinose, fucose, and ribose. These cis-hydroxy sugars, sugar polymers and sugar derivatives may also exist in microbial cell wells, such as in certain yeasts and other fungi, as well as in specific gums, such as xanthan, pectin and guar gums. The trans-hydroxy sugars, and sugar derivatives which have little or no apparent affinity for microbial pathogen surfaces include such materials as glucose, glucosamine, xylose, fructose, cellulose, and starch. Carbohydrate materials which are composed of both cis- and trans-hydroxy sugars, such as the galactose/glucose disaccharide lactose, will have a lesser adsorptive capacity.

The present invention for reducing intestinal pathogens is based on the discovery that cis-hydroxy sugars and compounds which contain these structures preferentially and competitively bind to pathogen sites, thereby minimizing the numbers of bacteria which would otherwise adhere to intestinal surfaces. As a result of this discovery certain cis-hydroxy sugar-containing structures have now been identified that are more effective and economical in reducing intestinal pathogen levels than the various simple sugars or whole yeast cells which have hitherto been known to effect such reduction. They are also more economical to include in commercial animals feeds. Included in this group of newly-defined materials are the complex carbohydrates which are comprised primarily of the cis-hydroxy sugars, such as the natural and bacterially-elaborated gums and other materials of vegetable origin. Examples of such materials are guar and xanthan gums and pectin. Their levels of inclusion in animal feeds is generally at about the 0.1% to about the 1.0% level.

Other objects and features of the present invention will be apparent to those skilled in the art. The following detailed description of the present invention is intended as a means of illustrating and defining certain preferred embodiments of the present invention and is not intended as a means of limiting, or defining the fully scope of the claimed invention.

DETAILED DESCRIPTION OF THE PRESENT INVENTION

A consideration of the chemicals structures of the following sugars and sugar-containing materials which have shown some level of efficacy in reducing adhesion of bacterial pathogens to intestinal mucosa of animals has led to the discovery that they appear to possess a common feature.

| Galactose | Galactosamine | Fucose |
|---|---|---|
| Mannose | Lactose | Arabinose |
| Yeasts (which generally contain mannose and/or galactomannose polymers in their cell walls) | | |

The common feature is the steric relationship between the hydroxy (OH) functions on at least two adjacent carbon atoms of the sugar ring structure. In all cases the OH groups project in the same direction, termed "cis" for the purposes of this description, either above or below ring structure. The ring structure is not co-planar, but may exist in either a "chair" or "boat" form. Nonetheless for the purpose of this description, the following diagrams illustrate the cis relationship of the hydroxy functions in those materials. The OH groups occupy the positions that are numbered either 2,3 or 3,4 in these ring structures, or in the case of ribose positions 1,2, and 3.

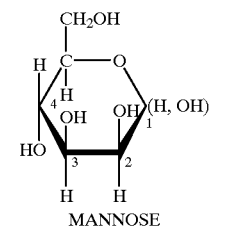

MANNOSE

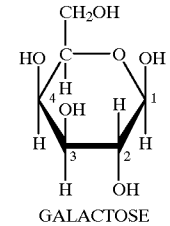

GALACTOSE

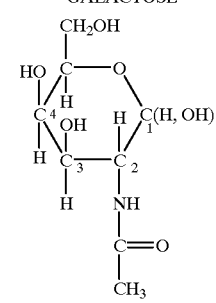

ACETYLGALACTOSAMINE

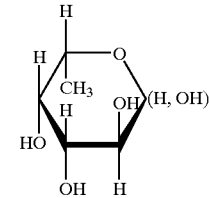

L-Fucose
FUCOSE

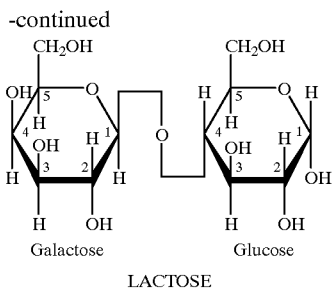
Galactose — Glucose
LACTOSE

It should be noted that lactose is a disaccharide, composed of galactose and glucose, which are, respectively, cis- and trans-hydroxy sugars. When 2.5% of lactose, arabinose or galactose were fed to two-day old chicks that had been orally inoculated with *Salmonella typhimurium*, only arabinose and galactose were found to statistically reduce Salmonella recoveries from the chicks' ceca through 21 days, but lactose failed to reduce it after 14 days. This lesser ability may be attributable to the cis- and trans- relationships of the OH groups in the lactose sugars.

The success of yeasts in reducing Salmonella retention in the intestinal tracts of poultry is also attributable to the presence in yeast cell walls of polymers of mannose (mannans) and, in some cases, galactomannans. The virtue of using yeasts in place of soluble sugars is that the latter are too water soluble to be adequately retained in the intestinal tracts of animals. A major portion of the dietary sugars (2.5% in one study) are absorbed gastrointestinally prior to reaching the ileal and cecal areas where their effects would be manifest. Yeasts, being insoluble, can survive the GI transit to a greater degree and provide the necessary adsorptive effects of the cis-sugar polymers in their cell walls. However, a major deficiency associated with the use of whole yeast cells is that they contain the yeasts' cellular contents, the inert bulk of which acts to dilute the impact of the yeast's cell wall activity. This inventor reasoned that the dietary inclusion of just yeast cell walls would be a more weight-efficient means of reducing pathogenic bacterial populations of the poultry intestinal flora.

It was then realized that such polymeric structures exist in a more purified form, such as in certain common food gums and related vegetable matter. Guar gum, for example, is a plant extract for human use, that is comprised of chains of (1→4)-B-D-mannose units with pendant (1→6)-a-D-galactose units. Xanthan gum, a polysaccharide produced by the microorganism *Xanthomonas campestris*, has a polymer backbone of (1→4)-B-D-glucose, with mannose and glucuronic acid in a 2:1 ratio in its side chains, as follows:

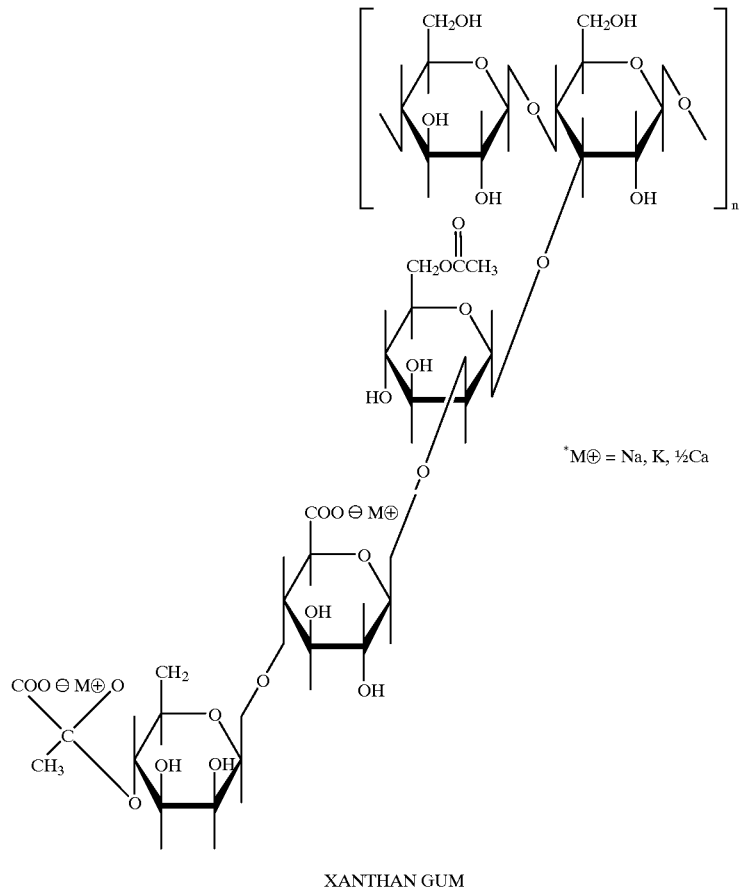
XANTHAN GUM

There are other food gums which are of potential value in this application, on the basis of their content of cis-hydroxy sugar components. These include, but are not limited to, gum tragacanth, comprised primarily of a polygalacturonic acid polymer; gum ghatti, comprised primarily of cis-OH sugars polymerized in a 10:6:2:1:2 ratio of arabinose/galactose/mannose/xylose/glucuronic acid, respectively; gum arabic, a polymer comprising arabinose/galactose/rhamnose/xylose/glucuronic acid; algin gum, a polymannuronic acid; and carrageenan, comprised galactopyranosyl sulfate ester polymers. Other vegetable extracts, such as pectin, have appropriately structural conformations. Pectin is primarily a polygalacturonic acid polysaccharide chain. It is also to be expected that agar, an algal extract, would serve effectively to reduce pathogen colonization of animal viscera. Agar is primarily a sulfated polygalactan, ordinarily unmetabolized by a variety of bacteria, thus its use in microbial cultures.

In contrast, the trans-OH sugars and polymers comprised primarily thereof do not have the spatial OH group configurations to act as adsorptive sites for bacterial pathogen receptors. Glucose is a prime example of a trans-OH sugar, and is the sole component of such common polymers as starch and cellulose. The structures of both glucose and its cellulose polymer are:

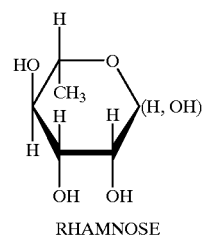
RHAMNOSE

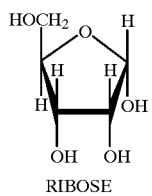
RIBOSE

This discovery would also suggest that polymers will lesser amounts or ratios of cis-OH sugars would function less effectively than higher content cis-OH sugar materials, as has already been noted for the cis-/trans- sugar lactose.

The level of dietary incorporation of these carbohydrate-based agents is generally dictated by the relative level and position of cis-OH sugar present in the structure, and its water solubility. There is an inverse relationship between the amount of cis-OH sugar in the structure and the amount necessary to provide maximum effectiveness. Positionally, the more sterically accessible the vicinal hydroxy pair is to the bacterial surface the less material is required. High water solubility reduces effectiveness resulting from dissolution and trans-mucosal absorptive losses of the material prior to reaching the relevant cecal and ileal sites. Excess dietary incorporation of insoluble, gelatinous gums can lead to

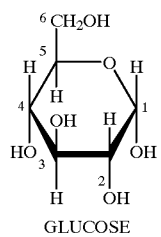
GLUCOSE

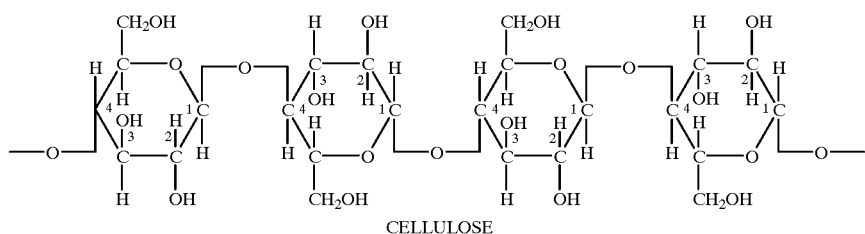
CELLULOSE

Evidence for the fact that cellulose and starch, respectively B- and a- (1→4)-glucose polymers, do not serve as adsorptive sites for bacterial pathogens can be deduced from the fact that these two polymers are high-level components of virtually all of the vegetable matter that forms the diet of domestic animals.

It can also be projected, from this inventive discovery regarding the adsorptive capacity of cis-sugars, that other simple sugars thusfar untested would function effectively in reducing pathogen colonization of animal intestinal tracts. Such monosaccharides would include rhamnose and ribose, whose structures are:

intestinal obstruction and poor transit of the bolus through the tract, which will have a negative effective on food utilization, as well as animal health and growth. In general the dietary incorporation of cis-OH sugar materials ranges from about 0.1% to about 2%, with a lower range of about 0.1% to about 1.0% for polymeric sugars such as in gums and vegetable extracts, and about 1.0% to about 2.0% for the simple sugars such as ribose and rhamnose that are of projected utility on the basis on the inventive discovery described herein.

The following examples illustrate the inventive concept, in accordance with and revealed in this patent, regarding the competitive affinity of cis-OH sugars and cis-OH sugar-containing materials for human pathogenic bacterial surfaces, in order to reduce intestinal retention of these bacteria. It is to be understood that these examples are provided by way of illustration only, and nothing therein should be taken as a limitation upon the overall scope of the invention.

EXAMPLE 1

This example illustrates the in-vitro affinity of guar gum, a cis-OH, mannose- and galactose-containing polysaccharide for the human pathogen *Salmonella choleraesuis* (ATCC 14028). A 1.0 ml inoculum containing $8.0\times10^7$ organism cfu's/ml was added to 100 ml of a 0.1% dispersion of guar gum in 0.85% saline. A similar inoculum was made into 100 ml of a 1.0% dispersion of chitin, a trans-OH natural product based on the polymeric glucose derivative N-acetyl-D-glucosamine. A similar inoculum was also made into 100 ml of a control solution of 0.85% saline. Upon introduction of the Salmonella inoculum into the guar gum dispersion, which was otherwise stable, an immediate precipitation of some dispersion was noted, while the solution retained some turbidity. In contrast, similar inoculation of both the chitin dispersion and the saline solution caused no immediate effect. Slow settling of the unstable chitin suspension took place over the next 24 hours, paralleling that observed for an uninoculated chitin control. No changes were seen in the saline control.

The 24-hour aged suspensions and dilutions were assayed for Salmonella organisms, by serial dilution and pour plating onto trypticase soy agar. The results, shown below, indicate at least a 100-fold greater retention of the organism in the aqueous phase of the 0.1% guar gum than in either the chitin suspension or the saline control. The settling out of the organism, that was observed in the latter two systems, did not occur in the guar system, presumably because of the affinity of the organism for the cis-OH mannose and/or galactose units in the polymer chain.

Salmonella Levels in Aqueous Phase

| 0.1% Guar Gum in 0.85% Saline | 1.0% Chitin in 0.85% Saline | 0.85% Saline |
|---|---|---|
| | cfu/ml | |
| $3.0\times10^7$ | $3.7\times10^5$ | $5.3\times10^5$ |

EXAMPLE 2

This example demonstrates the in-vivo affinity of guar gum, evaluated in Example 1, and xanthan gum, a food gum with mannose units on a glucose-polymer backbone, to reduce *Salmonella typhimurium* colonization of chicks that had been inoculated with log 7.5 cfu/chick on day 4 post-hatch. The guar gum was incorporated into the feed at two levels, 3.3 gms and 16.5 gms/ kg of feed, and the xanthan gum only at 3.3 gms/kg. A control group was also run. The chicks were grown in isolation units, with continuous access to the feed. Duplicate analyses of the cecal contents of 20 chicks were carried out, per treatment, after both Day 10 and Day 23. Bird weights were recorded at both time intervals, and feed efficiencies (FCR values) calculated for each treatment after Day 23. The results were as follows:

| TREATMENT | Mean Log Salmonella/gm (ceca) | | Mean % Salmonella Positive Ceca | | Bird Weights (gms) | | FCR |
|---|---|---|---|---|---|---|---|
| GROUP | Day 10 | Day 23 | Day 10 | Day 23 | Day 10 | Day 23 | Day 23 |
| Control, Standard Feed | 1.92 | 2.41 | 55 | 55 | 191.6 | 806.1 | 1.94 |
| Guar Gum 3.3 gm/kg Feed | 0.50⁺ | 0.71* | 25 | 20 | 194.8 | 773.9 | 1.75 |
| Xanthan Gum 3.3 gm/kg Feed | 2.10 | 1.17⁺ | 55 | 25 | 209.9⁺ | 797.5 | 1.74 |
| Guar Gum 16.5 gm/kg Feed | 2.20 | 3.20 | 50 | 80 | 184.4 | 602.8⁺ | 2.38* |

*Significantly different from control ($P < 0.05$)
⁺Significantly different from control ($P < 0.10$)

Significant reductions were noted (1.7 logs by Day 23, $P<0.05$) in Salmonella colonization of broiler chicks treated with guar gum at 3.3 gm/kg of feed (0.33% in the diet). A trend towards improved feed efficiency is also noted.

The higher level of guar gum (1.65% in the diet) probably resulted in intestinal blockage, and therefore elevated Salmonella population levels, decreased bird weights and feed efficiencies.

The xanthan gum led to lower cecal colonization through Day 23, though less so than for the guar gum. Feed efficency also appears to be improved in comparison with the controls.

It may be noted that the guar gum, predominating in the cis-OH sugars mannose and galactose, performed better than the xanthan gum, which contains mannose units on a (trans-OH) glucose chain background.

EXAMPLE 3

This example demonstrates the in-vivo ability of guar gum to reduce both Salmonella levels and the incidence of intestinal colonization in newly-hatched chicks that were environmentally exposed to the organism throughout the subsequent 6-weeks. The guar gum was incorporated into the feed at 2.25 kg/ton (0.248%). A control group was also run. The chicks were grown in duplicate pens, with continuous access to the feed. Exposure to *Salmonella typhimurium* was via 4 seeder chicks in each pen that had been previously inoculated with the organism. Duplicate analyses of the cecal contents of 10 chicks were carried out, per treatment, after Weeks 2, 4, and 6. Feed Conversion Ratios (FCR values) were also calculated after Week 6. The tabulated results were:

Effect of Guar Gum in feed on cecal Salmonella population in broilers

| Floor Pen # | Feed Treatment | Log Salmonella cfu/gm ceca/cecal contents (n = 10 birds/pen/week) | | | | | |
|---|---|---|---|---|---|---|---|
| | | Week 2 | | Week 4 | | Week 6 | |
| | | Pen | Mean | Pen | Mean | Pen | Mean |
| 11 | Pos. Contr./Std. Feed | 0.73 | 1.65 | 0.43 | 0.57 | 0.10 | 0.20 |
| 24 | Pos. Contr./Std. Feed | 2.56 | | 0.70 | | 0.30 | |
| 1 | Guar, 0.248% in Feed | 1.16 | 1.13 | 0.20 | 0.15 | 0.20 | 0.10 |
| 14 | Guar, 0.248% in Feed | 1.10 | | 0.10 | | 0.00 | |

Effect of Guar Gum in feed on frequency of cecal Salmonella colonization

| Floor Pen # | Feed Treatment | % Salmonella positive ceca/cecal contents (n = 10 birds/pen/week) | | | | | |
|---|---|---|---|---|---|---|---|
| | | Week 2 | | Week 4 | | Week 6 | |
| | | Pen | Mean | Pen | Mean | Pen | Mean |
| 11 | Pos. Contr./Std. Feed | 20 | 50 | 40 | 40 | 10 | 20 |
| 24 | Pos. Contr./Std. Feed | 80 | | 40 | | 30 | |
| 1 | Guar, 0.248% in Feed | 60 | 60 | 20 | 15 | 20 | 10 |
| 14 | Guar, 0.248% in Feed | 60 | | 10 | | 0 | |

Effect of Guar Gum on estimated feed conversion ratio (FCR)

| Floor Pen # | Feed Treatment | Pen FCR | Mean FCR |
|---|---|---|---|
| 11 | Pos. Contr./Std. Feed | 2.52 | 2.40 |
| 24 | Pos. Contr./Std. Feed | 2.27 | |
| 1 | Guar, 0.248% in Feed | 1.80 | 2.15 |
| 14 | Guar, 0.248% in Feed | 2.49 | |

The results of this study indicate that there is both a reduction in the levels and in the frequency of Salmonella colonization in broiler chicks that had ingested standard feed containing 0.248% guar gum, over the 6-week growout period. A trend toward improved feed efficiencies was observed, but the differences are not statistically significant owing to the limited number of samples analyzed and the use of mixed-sex chicks.

What is claimed is:

1. An animal feed composition for reducing colonization of animal intestines by Salmonella and other bacterial pathogens, consisting essentially of:
   a polysaccharide containing a cis-hydroxy sugar unit or a derivative thereof; and,
   an animal feed in combination with said polysaccharide.

2. The animal feed composition according to claim 1, wherein said cis-hydroxy sugar unit is a member selected from the group consisting of mannose, a mannose derivative, galactose, a galactose derivative, galactomannans, galactosamine, fucose, arabinose and a combination thereof.

3. The animal feed composition according to claim 1, further comprising a monosaccharide containing a cis-hydroxy sugar unit selected from the group consisting of ribose, a derivative of ribose, rhamnose, a derivative of rhamnose and a combination thereof.

4. The animal feed composition according to claim 1, wherein said cis-hydroxy sugar unit is included in said animal feed composition in the form of a biopolymer.

5. The animal feed composition according to claim 4, wherein said biopolymer is a food gum.

6. The animal feed composition according to claim 4, wherein said biopolymer is a member selected from the group consisting of guar gum, xanthan gum, pectin, gum tragacanth, gum arabic, algin, carrageenan and a combination thereof.

7. The animal feed composition according to claim 4, wherein said biopolymer is approximately 0.1% to approximately 1.0%, by weight, of said animal feed composition.

8. An animal feed composition for reducing colonization of animal intestines by Salmonella and other bacterial pathogens, consisting essentially of:
   a cis-hydroxy monosaccharide sugar selected from the group consisting of ribose, a derivative of ribose, rhamnose, a derivative of rhamnose and a combination thereof; and,
   an animal feed in combination with said monosaccharide sugar.

9. The animal feed composition according to claim 8, further comprising a polysaccharide containing a cis-hydroxy sugar unit or a derivative thereof, wherein said cis-hydroxy sugar unit is a member selected from the group consisting of mannose, a mannose derivative, galactose, a galactose derivative, galactomannans, galactosamine, fucose, arabinose and a combination thereof.

10. The animal feed composition according to claim 9, wherein said cis-hydroxy sugar unit is included in said animal feed composition in the form of a biopolymer.

11. The animal feed composition according to claim 10, wherein said biopolymer is a food gum.

12. The animal feed composition according to claim 10, wherein said biopolymer is a member selected from the group consisting of guar gum, xanthan gum, pectin, gum tragacanth, gum arabic, algin, carrageenan and a combination thereof.

13. The animal feed composition according to claim 10, wherein said biopolymer is approximately 0.1% to approximately 1.0%, by weight, of said animal feed composition.

14. An animal feed composition for reducing colonization of animal intestines by Salmonella and other bacterial pathogens, consisting essentially of:
   a polysaccharide containing two cis-hydroxy sugar units or derivatives thereof; and,
   an animal feed in combination with said polysaccharide.

15. The animal feed composition according to claim 14, wherein said cis-hydroxy sugar units are a members independently selected from the group consisting of mannose, a mannose derivative, galactose, a galactose derivative, galactomannans, galactos-amine, fucose, arabinose and a combination thereof.

16. The animal feed composition according to claim 14, further comprising a monosaccharide containing two cis-hydroxy sugar units independently selected from the group consisting of ribose, a derivative of ribose, rhamnose, a derivative of rhamnose and a combination thereof.

17. The animal feed composition according to claim 14, wherein said cis-hydroxy sugar units are included in said animal feed composition in the form of a biopolymer.

18. The animal feed composition according to claim 17, wherein said biopolymer is a food gum.

19. The animal feed composition according to claim 17, wherein said biopolymer is a member selected from the group consisting of guar gum, xanthan gum, pectin, gum tragacanth, gum arabic, algin, carrageenan and a combination thereof.

20. The animal feed composition according to claim 17, wherein said biopolymer is approximately 0.1% to approximately 1.0%, by weight, of said animal feed composition.

* * * * *